(12) United States Patent
Bardell et al.

(10) Patent No.: US 6,674,525 B2
(45) Date of Patent: Jan. 6, 2004

(54) SPLIT FOCUSING CYTOMETER

(75) Inventors: Ronald Bardell, Redmond, WA (US); Bernhard H. Weigl, Seattle, WA (US); C. Frederick Battrell, Redmond, WA (US)

(73) Assignee: Micronics, Inc., Redmond, WA (US)

( * ) Notice: Subject to any disclaimer, the term of this patent is extended or adjusted under 35 U.S.C. 154(b) by 0 days.

(21) Appl. No.: 10/114,790

(22) Filed: Apr. 3, 2002

(65) Prior Publication Data

US 2002/0149766 A1 Oct. 17, 2002

Related U.S. Application Data

(60) Provisional application No. 60/281,114, filed on Apr. 3, 2001.

(51) Int. Cl.[7] .................................................. G01N 1/10
(52) U.S. Cl. ...................... 356/246; 356/39; 422/82.05; 422/102
(58) Field of Search ................................. 356/244, 246, 356/335–343, 39, 43; 422/82.05, 82.09, 100, 101, 102, 55, 69; 210/96.1, 511, 634; 204/452, 651

(56) References Cited

U.S. PATENT DOCUMENTS

| | | | |
|---|---|---|---|
| 4,352,558 A | 10/1982 | Eisert | 356/39 |
| 5,032,381 A | 7/1991 | Bronstein et al. | 424/9 |
| 5,726,751 A | * | 3/1998 | Altendorf et al. | 356/246 |
| 5,858,187 A | * | 1/1999 | Ramsey et al. | 204/452 |
| 5,932,100 A | * | 8/1999 | Yager et al. | 422/55 |
| 6,067,157 A | * | 5/2000 | Altendorf | 356/337 |
| 6,120,666 A | * | 9/2000 | Jacobson et al. | 422/68.1 |
| 6,171,865 B1 | 1/2001 | Weigl et al. | 436/52 |
| 6,416,642 B1 | * | 7/2002 | Alajoki et al. | 422/100 |
| 6,424,415 B1 | * | 7/2002 | Kasdan et al. | 356/246 |
| 6,488,896 B2 | * | 12/2002 | Weigl et al. | 422/101 |

OTHER PUBLICATIONS

U.S. patent application Ser. No. 99/60397, Holl et al., filed Apr. 1999.*

Scampavia, L.D., "A Coaxial Jet Mixer for Rapid Kinetic Analysis in Flow Injection and Flow Injection Cytometry," *Analytical Chemistry* 67(17): 2743–2749, Sep. 1, 1995.

* cited by examiner

*Primary Examiner*—Frank G. Font
*Assistant Examiner*—Sang H. Nguyen
(74) *Attorney, Agent, or Firm*—Seed Intellectual Property Law Group PLL

(57) ABSTRACT

A microcytometer which combines lysing and cytometry into a unified system that achieves blood lysis and white blood cell count in a single device. The device focuses the white cells into a thin ribbon which is then focused into a single stream for analysis.

9 Claims, 2 Drawing Sheets

SPLIT FOCUSING CYTOMETER

CROSS REFERENCE TO RELATED APPLICATIONS

This application claims benefit from U.S. Provisional Patent Application Serial No. 60/281,114, filed Apr. 3, 2001, which application is incorporated herein by reference.

BACKGROUND OF THE INVENTION

1. Field of the Invention

This invention relates generally to microfluidic devices for performing analytic testing, and, in particular, to a microcytometer which combines the functions of chemical reaction and particle focusing into a single structure.

2. Description of the Related Art

Microfluidic devices have recently become popular for performing analytic testing. Using tools developed by the semiconductor industry to miniaturize electronics, it has become possible to fabricate intricate fluid systems which can be inexpensively means produced. Systems have been developed to perform a variety of analytical techniques for the acquisition of information for the medical field.

Microfluidic devices may be constructed in a multi-layer laminated structure where each layer has channels and structures fabricated from a laminate material to form microscale voids or channels where fluid flow. A microscale channel is generally defined as a fluid passage which has at least one internal cross-sectional dimension that is less than 500 $\mu$m and typically between about 0.1 $\mu$m and about 500 $\mu$m. The control and pumping of fluids through these channels is affected by either external pressurized fluid forced into the laminate, or by structures located within the laminate.

U.S. Pat. No. 5,716,852 teaches a method for analyzing the presence and concentration of small particles in a flow cell using diffusion principles. This patent, the disclosure of which is incorporated herein by reference, discloses a channel cell system for detecting the presence of analyte particles in a sample stream using a laminar flow channel having at least two inlet means which provide an indicator stream and a sample stream, where the laminar flow channel has a depth sufficiently small to allow laminar flow of the streams and length sufficient to allow diffusion of particles of the analyte into the indicator stream to form a detection area, and having an outlet out of the channel to form a single mixed stream. This device, which is known at a T-Sensor, may contain an external detecting means for detecting changes in the indicator stream. This detecting means may be provided by any means known in the art, including optical means such as optical spectroscopy, or absorption spectroscopy of fluorescence.

U.S. Pat. No. 5,932,100, which patent is also incorporated herein by reference, teaches another method for analyzing particles within microfluidic channels using diffusion principles. A mixture of particles suspended in a sample stream enters an extraction channel from one upper arm of a structure, which comprises microchannels in the shape of an "H". An extraction stream (a dilution stream) enters from the lower arm on the same side of the extraction channel and due to the size of the microfluidic extraction channel, the flow is laminar and the streams do not mix. The sample stream exits as a by-product stream at the upper arm at the end of the extraction channel, while the extraction stream exits as a product stream at the lower arm. While the streams are in parallel laminar flow is in the extraction channel, particles having a greater diffusion coefficient (smaller particles such as albumin, sugars, and small ions) have time to diffuse into the extraction stream, while the larger particles (blood cells) remain in the sample stream. Particles in the exiting extraction stream (now called the product stream) may be analyzed without interference from the larger particles. This microfluidic structure, commonly known as an "H-Filter," can be used for extracting desired particles from a sample stream containing those particles.

Flow cytometry is a sensitive and versatile probe of the optical characteristics of microscopic biological particles, with widespread applications including hematology, immunology, genetics, food science, pharmacology, microbiology, parasitology and oncology. Optical flow cytometers use light scattering and fluorescence to determine physical and chemical properties of the particles. For measurement, particles are arranged in single file, typically by hydrodynamic focusing within a sheath fluid, and interrogated by a light beam propagating orthogonal to the flow axis. Scattered light is measured in a near forward direction by a photodetector. In addition, a second photodetector is often positioned at 90° to the forward scattering direction to collect large angle scattering and fluorescence.

Existing commercial cytometers are large and complicated instruments requiring skilled operators. To increase the accessibility of flow cytometry, microfabricated flow cells and compact cytometers are desired. In a microfabricated flow channel, a challenge is to get illuminating light into the channel and get both forward scattered and 90° scattered light out of the channel. A few microfabricated flow cytometer flow channels have been reported. Miyake et al. [Proceedings of the IEEE Micro Electro Mechanical Systems Workshop, pp. 265–270, Nara, Japan, January 1991] describe a micromachined sheath flow channel made of five stacked plates. Three metal plates are used to crate a flow having a sample core within a sheath, and glass plates on the top and bottom of the stack provide optical access to the flow channel for illumination through the top and forward scattered light collection through the bottom. Ninety degree scattering cannot be collected. Sobek et al. [Proceedings of the IEEE Micro Electro Mechanical Systems Workshop, pp. 219–224, Fort Lauderdale, Fla., February 1993] describe a four-layer silicon microfabricated hexagonal sheath flow channel. The channel is formed between two of the silicon wafers. Integrated optical waveguides intersecting the channel are used to couple laser light into the channel and out of the channel in the forward direction. At this intersection, the top and bottom walls of the channel are silicon nitride/ silicon dioxide windows for 90° light collection. Each window is fabricated by growing an oxide layer on a silicon wafer, bonding the oxide layer to a second silicon wafer, etching away the silicon on both sides of the oxide at the window region and depositing a nitride layer. Sobek et al. [Proceedings of the Solid-State Sensors and Actuators Workshop, Hilton Head, S.C., June 1994] describe a sheath flow channel fabricated between tow fused silica wafers. To couple light into the channel and out in the forward direction, optical fibers are sandwiched between the wafers orthogonal to the flow axis. Fluorescence is collected through the upper transparent wafer.

U.S. Pat. No. 5,726,751 describes a silicon microchannel optical flow cytometer. This cytometer uses two components: a flow cytometer optical head and disposable flow module. The flow module utilizes a V-groove flow channel micromachined in a silicon wafer. The optical head comprises a laser to provide as illuminating beam and a small and large angle photodetectors.

U.S. Pat. No. 5,561,517 describes a device for flow type particle image analysis in which, for any given sample to be analyzed, a timing signal for the light emission of a pulse light source is generated in every field image reading out period.

U.S. Pat. No. 5,728,582 describes a type particle image analysis method and apparatus which facilitates the correlation between particles obtained by a particle detection unit and particle images obtained by a particle image pick-up unit.

While the devices and methods described can be used for particle image analysis, there is no cytometer upon which an analysis can be performed quickly and easily using a simple disposable cartridge.

SUMMARY OF THE INVENTION

It is therefore an object of the present invention to provide a microcytometry structure that combines the functions of chemical reactions and particle focusing.

It is a further object of the present invention to provide a microcytometer that can be placed on a disposable plastic card.

It is a still further object of the present invention to provide a microcytometer which uses multiple focusing structures to create a core consisting of a single file of cells.

These and other objects of the present invention will be more readily apparent from the description and drawings that follow.

DETAILED DESCRIPTION OF THE PREFERRED EMBODIMENT

The present invention is directed to a microfluidic device for analyzing particles dispersed in a sample fluid, comprising a first microfluidic structure having a first and second inlet, a first reactor channel, a third inlet located downstream from said reactor channel, and a detection region such that said sample enters though said first inlet into said reactor channel, and a first reagent fluid enters though said second inlet into said reactor channel such that said sample fluid is being contacted by said first reagent fluid on at least one side and that at least one dimension of said sample fluid is reduced by being hydrodynamically or geometrically focused, said sample fluid flowing in a thin ribbon next to said reagent fluid in said reactor channel, and a second fluid entering said reactor channel though said third inlet such that said ribbon of sample fluid is further focused into a thin core essentially comprising a single file of particles, and flowing said core past said detection region.

Figure 1:
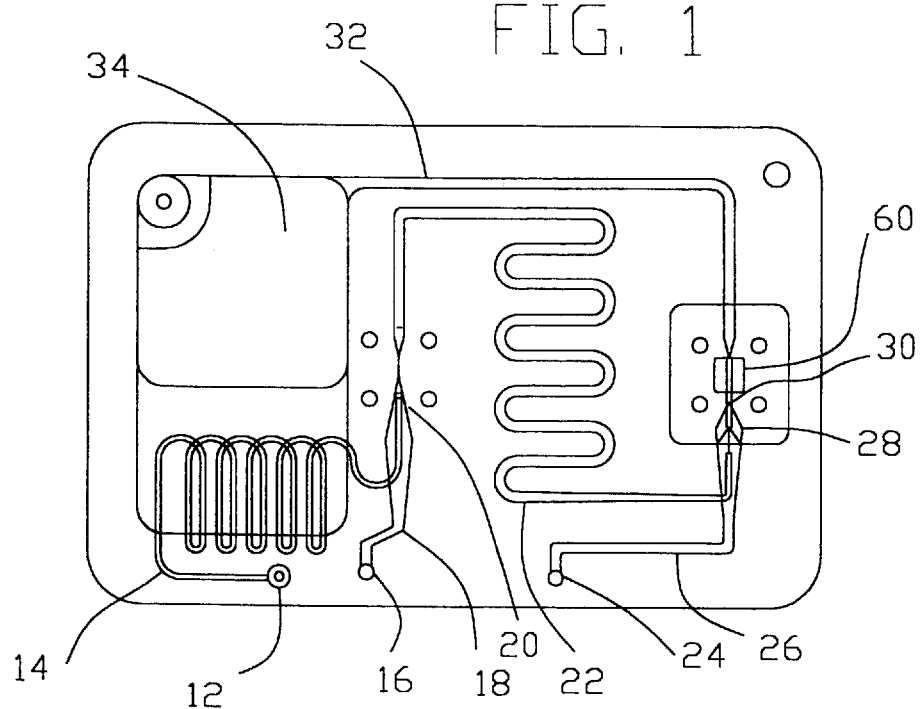
FIG. 1 is a plan view of a microcytometer according to the present invention.
Figure 2:
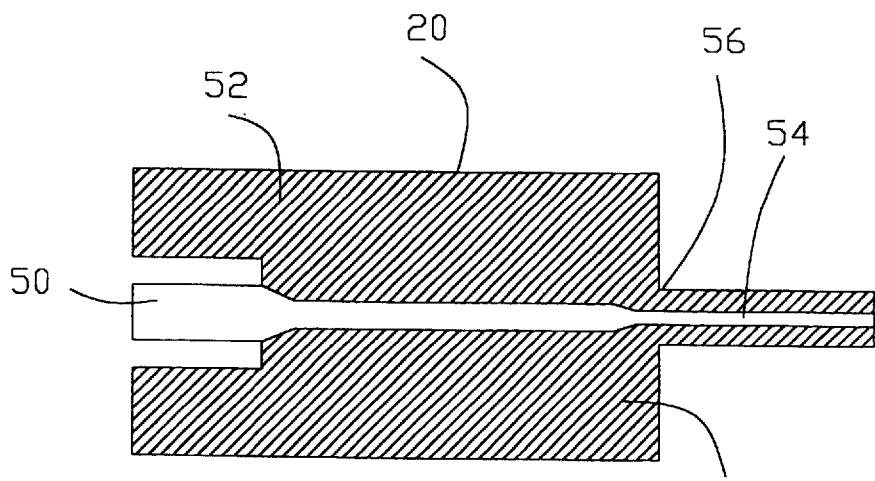
FIG. 2 is a side view of the lyse injector of the present invention.

As shown in FIGS. 1 and 2, a microfluidic device 10 for analyzing particles dispersed in a sample fluid 50, comprises a microfluidic structure having a first inlet 12 coupled to a first channel 14, a second inlet 16 coupled to a second channel 18, an injector 20, a reactor channel 22, a third inlet 24 coupled to a third channel 26 located downstream from reactor channel 22, a focusing chamber 28, a cytometer channel 30 and a detection region 60. During operation, sample fluid 50 and a first reagent fluid 52 are introduced though first inlet 12 and second inlet 16, respectively, into first and second channels 14 and 16, respectively. Streams of sample fluid 50 and first reagent fluid 52 flow through first and second channels 14 and 16 into injector 20 and reactor channel 22 such that the stream of sample fluid 50 is focused, in one dimension (i.e., widthwise or depthwise), into a thin ribbon 54 between two streams of first reagent fluid 52. Ribbon 54 and the two streams of first reagent fluid 52 flow though reactor channel 22 into focusing chamber 28. At the same time, a sheath fluid is introduced though third inlet 24 and third channel 26 into focusing chamber 28 such that ribbon 54 is further focused, in a second dimension (i.e., widthwise or depthwise), into a single file stream of particles between two streams of the sheath fluid, which then flows through cytometer channel 30 past detection region 60.

In a more specific embodiment, and referring again to FIG. 1, microfluidic device 10 is a microcytometer cartridge. Cartridge 10 contains a whole blood inlet 12 which is coupled to a channel 18. A lyse inlet 16 is coupled to a channel 18. Channels 14 and 18 come together at a lyse injector 20. The output of lyse injector 20 is connected to a lyse channel 22. A sheath inlet 24 is coupled to a channel 26 which meets up with lyse channel 22 at a focusing chamber 28. The output of chamber 28 leads into a cytometer channel 30 where the cells are interrogated. Channel 30 is coupled to an exit channel 32 which leads to a waste chamber 34.

Figure 3:
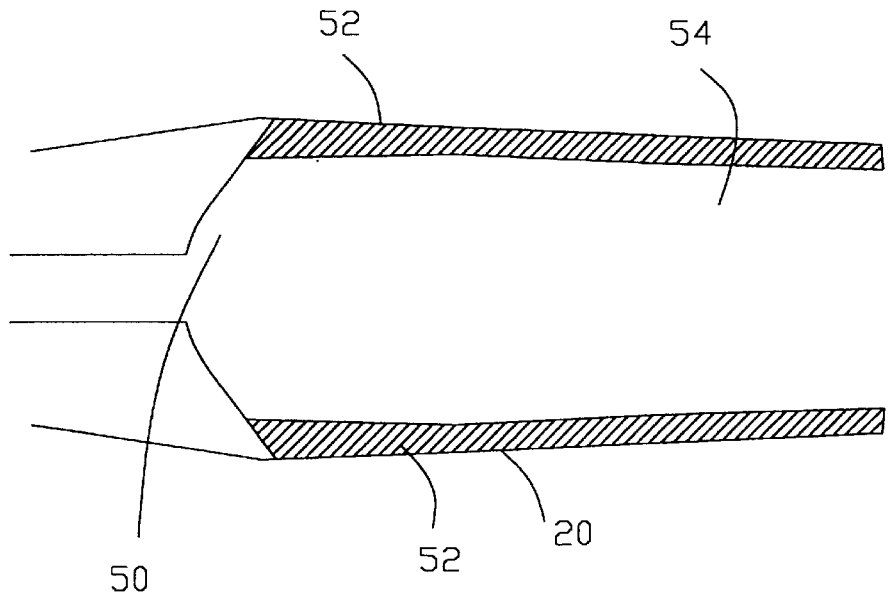
FIG. 3 is a top view of the injector of FIG. 2.

The operation of cartridge 10 will now be disclosed. A sample 50 of whole blood is loaded into inlet 12, where it travels through channel 14. At the same time, a lyse reagent 52, such as regular water, is loaded into inlet 16 where it travels through channel 18. At lyse injector 20, the whole blood sample 50 is surrounded by lyse reagent 52 and focused into a thin ribbon 54, as can be seen in FIGS. 2 and 3. As lyse reagent 52 forms two high pressure streams above and below sample 50, which is flowing at a lower pressure, ribbon 54 is formed. During this process, the red blood cells within sample 50 rupture, leaving the white blood cells to continue on into lyse channel 22. Ribbon 54 is also geometrically focused when leaving injector 20, as the entrance 56 to channel 22 is narrower than the passageway through injector 20.

Ribbon 54 consisting of white blood cells travels through channel 22 to focusing chamber 28. At focusing chamber 28, a sheath fluid, which may be a solution such as phosphate buffered saline, which has been loaded into inlet 24 causes ribbon 54 to be focused such that a single file stream of white blood cells exits chamber 28 into cytometer channel 30. As the sheath fluid flows on either side of ribbon 54 at a much higher pressure, ribbon 54 is narrowed until the stream of single file white blood cells is created.

Figure 4:
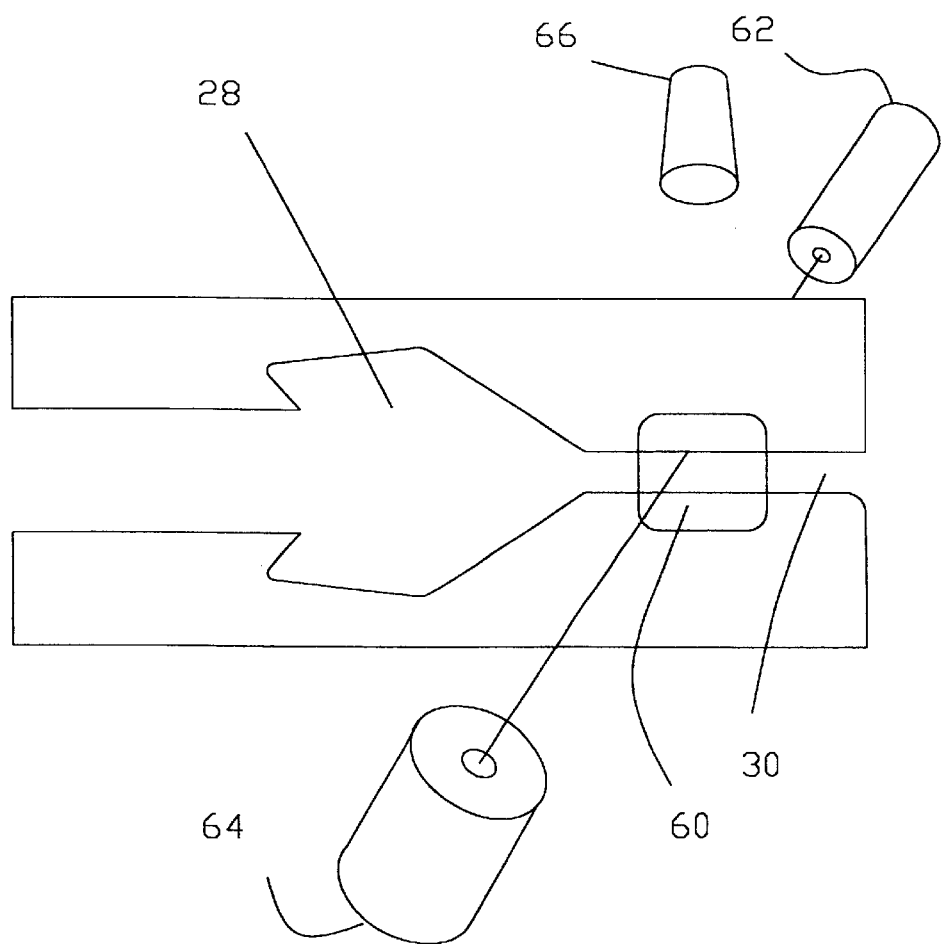
FIG. 4 is a plan view of the detector section of microcytometer of the present invention which also includes the external detection equipment.

As the white cell stream flows through channel 30, the stream passes through a window 60 where a laser source 62 is focused, as can be seen in FIG. 4. A light scatter detector 64 counts and classifies the particles, as does a fluorescence detector 66. The data accumulated by detectors 64 and 66 is stored for analysis. The cells then pass through channel 32 into waste chamber 34.

While the present invention has been shown and described in terms of a preferred embodiment thereof, it will be understood that this invention is not limited to this particular embodiment and that changes and medications may be made without departing from the true spirit and scope of the invention as defined in the appended claims.

What is claimed is:

1. A microfluidic device for analyzing particles dispersed in a sample fluid, comprising:
   a first inlet fluidically coupled to a first channel for introduction of the sample fluid;
   a second inlet fluidically coupled to a second channel for introduction of a first reagent fluid;
   a reactor channel fluidically coupled to the first channel and the second channel such that the sample fluid is focused into a thin ribbon between two streams of the first reagent fluid, the reactor channel having a length sufficient to allow a chemical reaction between the sample fluid and the first reagent fluid;
   a third inlet fluidically coupled to a third channel for introduction of a sheath fluid;
   a cytometer channel fluidically coupled to the reactor channel and the third channel such that the sample fluid is focused into a single file stream of particles between two streams of the sheath fluid; and
   a detection region.

2. The microfluidic device of claim 1, wherein:
   the sample fluid comprises whole blood;
   the particles are white blood cells; and
   the first reagent fluid comprises a lyse reagent.

3. The microfluidic device of claim 2 wherein the lyse reagent is water.

4. The microfluidic device of claim 2 wherein the sheath fluid is phosphate buffered saline.

5. The microfluidic device of claim 1 further comprising a waste chamber coupled to the cytometer channel.

6. A method for analyzing particles dispersed in a sample fluid, comprising:
   introducing the sample fluid and a first reagent fluid into a microfluidic device;
   focusing the sample fluid into a thin ribbon between two streams of the first reagent fluid;
   flowing the sample fluid and first reagent fluid through a reactor channel of the microfluidic device, the reactor channel having a length sufficient to allow a chemical reaction between the sample fluid and the first reagent fluid;
   introducing a sheath fluid into the microfluidic device;
   focusing the sample fluid into a single file stream of particles between two streams of the sheath fluid; and
   flowing the sample fluid, first reagent fluid and sheath fluid through a cytometer channel of the microfluidic device past a detection region of the microfluidic device.

7. The method of claim 6 wherein:
   the sample fluid comprises whole blood;
   the particles are white blood cells; and
   the first reagent fluid comprises a lyse reagent.

8. The method of claim 7 wherein the lyse reagent is water.

9. The method of claim 7 wherein the sheath fluid is phosphate buffered saline.

* * * * *